United States Patent [19]

McCombie

[11] 4,443,463

[45] Apr. 17, 1984

[54] (5R,6S,8R)-6-(1-HYDROXYETHYL)-2-(HYDROXYALKYLTHIO)-PENEM-3-CARBOXYLATES

[75] Inventor: Stuart W. McCombie, West Orange, N.J.

[73] Assignee: Scherling Corporation, Kenilworth, N.J.

[21] Appl. No.: 324,932

[22] Filed: Nov. 25, 1981

Related U.S. Application Data

[63] Continuation-in-part of Ser. No. 91,610, Nov. 5, 1979, abandoned, which is a continuation-in-part of Ser. No. 62,875, Aug. 1, 1979, abandoned, which is a continuation-in-part of Ser. No. 2,471, Jan. 10, 1979, abandoned.

[51] Int. Cl.$^3$ ................... C07D 499/00; A61K 31/425
[52] U.S. Cl. ............................. 424/270; 260/245.2 R
[58] Field of Search ................. 260/245.2 R; 424/270

[56] References Cited

U.S. PATENT DOCUMENTS 4,260,618  4/1981  Christensen et al. ............... 424/263
4,301,074  11/1981 Christensen et al. ........ 260/245.2 R

FOREIGN PATENT DOCUMENTS 2013674A  8/1979  United Kingdom.

Primary Examiner—Nicholas S. Rizzo
Attorney, Agent, or Firm—Anita W. Magatti; Bruce M. Eisen

[57] ABSTRACT

Sodium, Potassium, Phthalidyl and Pivalyloxymethyl (5R,6S,8R)-6-(1-hydroxyethyl)-2-(2-hydroxyethylthio)-penem-3-carboxylates exhibit potent, broad spectrum antibacterial activity, are orally effective and chemically stable.

10 Claims, No Drawings

(5R,6S,8R)-6-(1-HYDROXYETHYL)-2-(HYDROXYALKYLTHIO)-PENEM-3-CARBOXYLATES

This is a continuation-in-part of copending application Ser. No. 91,610, filed Nov. 5, 1979, now abandoned, which is a continuation-in-part of Ser. No. 62,875, filed Aug. 1, 1979, now abandoned which is a continuation-in-part of Ser. No. 2,471, filed Jan. 10, 1979, now abandoned.

This invention relates to (5R,6S,8R)-6-(1-hydroxethyl)-2-(hydroxyalkylthio)-penem-3-carboxylates.

More particularly, this invention relates to compounds of the formula:

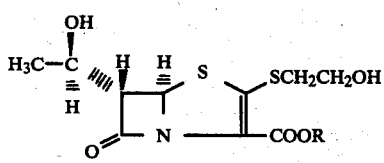

wherein R is a sodium or a potassium cation or a metabolisable ester group. These compounds are antibacterial agents.

The term "metabolisable ester" group denotes a pharmaceutically acceptable ester group which is metabolically removed in the body. Two particularly useful metabolisable ester groups are the phthalidyl group and the pivaloyloxymethyl group.

Certain processes produce these compounds as their racemic mixtures, i.e., a 5R,6S,8R compound is produced with its enantiomer (mirror image), i.e., a 5S,6R,8S compound, in equal amounts when the starting compound is a racemic mixture. The two enantiomers may be separated by conventional means, e.g., by resolution by fractional crystallizations of optically active salt forms, e.g., the salts derived from optically active amino acids, (−)-brucine, (+)- and (−)-ephedrine. Preferably, the chiral compounds of formula I are produced in their pure enantiomeric form by utilizing optically active intermediates in the synthetic procedure. These optically active intermediates may be produced by conventional resolution or by stereospecific synthesis according to the procedures of E.P.O. Published Application No. 0013662, the disclosure of which is hereby incorporated by reference. A preferred method of preparing the compounds of formula I, specifically described in the examples, utilizes procedures of Adriano Afonso and Frank Hon, U.S. Ser. No. 230,774, filed Feb. 2, 1980 (of common assignee as the instant application), the disclosure of which is incorporated herein by reference.

The designations of absolute spatial configuration are based on X-ray crystal analysis.

The compounds of this invention possess antibacterial activity of both the gram-positive and gram-negative type. Most importantly, they are orally active antibacterial agents which afford effective blood levels at pharmaceutically acceptable dosages. When tested in standarized microbiological assays, the compounds of this invention are active against such gram-positive organisms as *Staphylococcus epidermidis*, and *Bacillus subtilis*, and such gram-negative organisms as *E. coli* and Salmonella at test levels of 0.1 to 100 μg/ml. Additionally, they show activity against such organisms which produce beta-lactamases, e.g., penicillanase and cephalosporinase, indicating a resistance against these enzymes.

For instance, sodium (5R,6S,8R)-6-(1-hydroxyethyl) 2-(2-hydroxyethylthio)-penem-3-carboxylate and the corresponding potassium salts are active against Staphylococcus 7607010 at a test level of 0.5 μg/ml. When tested against *B. subtilis* 1119601 (a beta-lactamase-containing organism) these compounds exhibit activity at 0.06 g/ml.

Thus, the present invention includes within its scope pharmaceutical compositions comprising an antibacterially effective amount of a penem of formula I together with a compatible pharmaceutically acceptable carrier or coating. In the foregoing compositions, the compounds of this invention can be used alone or in combination with other antibacterial agents and/or enzyme inhibitors.

Also included within this invention is the method of effectively treating a warm-blooded animal having a susceptible bacterial infection which comprises administering to said animal a non-toxic, antibacterially effective amount of a penem of formula I. A preferred pharmaceutical composition is an oral dosage form comprising an antibacterially effective amount of a compound of formula I.

A particularly preferred embodiment relates to a pharmaceutical composition which is an oral antibacterial dosage unit comprising a compound of formula I. in an amount sufficient to be orally effective as a broad spectrum antibacterial, together with a non-toxic pharmaceutically acceptable carrier and/or enzyme inhibitors. Of these compositions, those which are solid are particularly desirable.

The dosage administered of penems of this invention is dependent upon the age and weight of the animal species being treated, the exact mode of administration, and the type and severity of bacterial infection being prevented or reduced. Typically, the dosage administered per day will be in the range of 5 to 200 mg./kg. per day with 20 to 80 mg./kg. per day being preferred.

For oral administration, the compounds of this invention may be formulated in the form of tablets, capsules, elixiers or the like. Likewise, they may be admixed with animal feed. They may also be applied topically in the form of ointments, both hydrophilic and hydrophobic, in the form of lotions which may be aqueous, non-aqueous or of the emulsion type, or in the form of creams, or as suppositories.

The compounds of formula I may be utilized in liquid form such as solutions, suspensions, and the like for otic and optic use and may also be administered parenterally via intramuscular injection.

Of the compositions of this invention, the most preferred is an oral solid dosage unit comprising the phthalidyl or pivaloyloxymethyl ester of (5R,6S,8R)-6-(1-hydroxyethyl)-2-(2-hydroxyethylthio)penem-3-carboxylate in an amount sufficient to be orally effective as a broad spectrum antibacterial, together with a nontoxic pharmaceutically acceptable carrier.

The following example describes in detail the compounds of this invention and processes for their preparation. It will be apparent to those skilled in the art that may modifications, both of material and method may be practiced without departing from the spirit or scope of the invention.

Preparation A sets forth a method for preparing a reactant used in Step C.

Preparation A

ALLYL OXALYL CHLORIDE

Allyl alcohol (11.6 g.) is added dropwise with stirring to a cold (0° C.) solution of oxalyl chloride (25.4 g.) in dry ether (50 ml.) while maintaining the temperature of the reaction mixture 100°-112° C. and is then stirred overnight followed by removal of the solvent in a rotary evaporator. The resultant residue is distilled to yield allyl oxalyl chloride as a colorless liquid (16 g.), b.p. 68°-70° C./44 mm.

EXAMPLE 1

(A)

(3S,4R,5R)-3-(1-trichloroethoxycarbonyloxyethyl)-4-(2-hydroxyethylthiocarbothioylthio)-azetidin-2-one Dissolve 10 g. of methyl-(5R,6S,8R)-2-(2,2-dimethyl)-6-(1-trichloroethoxycarbonyloxyethyl)penam-3-carboxylate in 150 ml. of methylene chloride at 0°-5° C., and 7.36 ml. of sulfuryl chloride and stir for one hour at room temperature. Pour the reaction mixture into an excess of aqueous sodium bicarbonate with stirring. Separate the two liquid phases, dry the organic phase and evaporate to a residue. Dissolve the residue in 100 ml. of methylene chloride and treat with ozone at −78° C. until a blue color persists, then add 5 ml. of dimethyl sulfide to the reaction mixture at room temperature for one hour, then add to a stirred ice cold trithiocarbonate solution prepared from 10 ml. of beta-mercaptoethanol and 6 g. of potassium hydroxide in 200 ml. of 50% aqueous ethanol cooled to 0° C. and treated with 28 ml. of carbon disulfide. Allow the mixture of the chlorolactam and the trithiocarbonate solution to react at 0° C. for 45 minutes with stirring, then dilute with water. Extract the reaction mixture with methylene chloride, wash with aqueous sodium bicarbonate, dry over magnesium sulfate and evaporate to a residue. Chromatograph the residue on silica gel, eluting with an increasing concentration of ethyl ether in methylene chloride to 30%. Combine like fractions containing the title compound as determined by thin layer chromatography and evaporate to obtain, thereby the product of this step as a yellow oil.

Yield—8.1 g.

I.R. ($CH_2Cl_2$) 3550,1770,1750 cm−1.

(B)

(3S,4R,5R)-3-(1-trichloroethoxycarbonyloxyethyl)-4-[2-(t-butyldimethylsilyloxy)ethylthiocarbothioylthio]-azetidin-2-one Dissolve 7.07 g. of the product from Step A in a mixture 50 ml. of methylene chloride and 1.43 ml. of pyridine, 2.64 g. of t-butylchlorodimethylsilane and 0.1 g. of imidazole. Stir the solution at room temperature for two days, wash with water and evaporate to a residue. Chromatograph the residue in silica gel using dichloromethane:hexane and then methylene chloride with increasing concentrations of ethyl ether. Combine like fractions containing the title compound as determined by thin layer chromatography and evaporate to obtain thereby, the title compound as a light yellow oil.

Yield—8.4 g.

I.R. 3400,1770, and 1750 cm−1.

(C)

Allyl-(5R,6S,8R)-2-[2-(t-butyldimethylsilyloxy)ethylthio]-6-(1-trichloroethoxycarbonyloxyethyl)-penem-3-carboxylate Dissolve 8.4 g. of the product of Step B in 50 ml. of methylene chloride containing 2.69 g. of allyl oxalyl chloride and stir at 0°-5° C. while adding 2.32 g. of diisopropylethylamine in 15 ml. of methylene chloride dropwise. Stir the reaction mixture for an additional half-hour at 0°-5° C., wash with water, with dilute hydrochloric acid and with dilute aqueous sodium bicarbonate. Dry the organic solvent phase over magnesium sulfate, filter and evaporate to a residue. Dissolve the residue in 100 ml. of ethanol-free chloroform, add 1.0 g. of calcium carbonate and reflux with stirring during the addition of 5 g. of triethyl phosphite over a 3-hour interval. Reflux the solution for an additional 18 hours, cool and chromatograph on silica gel eluting with methylene chloride:hexane, methylene chloride and finally with 1% ethyl ether in methylene chloride. Combine like fractions containing the title compound as determined by thin layer chromatography to obtain thereby the title compound as a yellowish oil. $^1$H NMR ($CDCl_3$): 0.10 (s,6), 0.92(s,9), 1.54 (d,3,J=7), 3.07(n,2), 3.84(m,3), 4.76(m,2), 4.79 (s,2), 5.1–5.6(m,3), 5.64(d,1,J-2.5) and 5.7–6.2 (m,1).5

(D)

Allyl-(5R,6S,8R)-2-(2-hydroxyethylthio)-6-(1-trichloroethoxycarbonyloxyethyl)-penem-3-carboxylate Dissolve 4.46 g. of the product of Step C in a mixture of 32 ml. of tetrahydrofuran, 4 ml. of water and 4 ml. of acetic acid. Stir the solution for 18 hours at room temperature with 2.4 g. of tetra-n-butylammonium fluoride. Pour the reaction mixture into a two-phase solvent system consisting of methylene chloride and water with stirring. Wash the organic phase with aqueous sodium bicarbonate. Dry the organic phase over magnesium sulfate, filter and evaporate to a residue. Chromatograph the residue on silica gel using ethyl ether:methylene chloride as the eluant. Combine like fractions containing the title compound as determined by thin layer chromatography and evaporate to obtain thereby the title compound of this example as a yellowish oil.

Yield—2.2 g.

$^1$H NMR ($CDCl_3$): 1.49(d,3,J=7),2.17)m,1,exch by $D_2O$)
3.12(m,Z),3.704.0(m,3),4.72(m,2),4.76(s,2),5.1–5.6(m,3)- ,5.67(d,2,J=2.5) and 5.7–6.2(m,1).

(E)

Allyl-(5R,6S,8R)-2-(2-hydroxyethylthio)-6-(1-hydroxyethyl)-penem-3-carboxylate

Dissolve 1.4 g. of the produce of Step D in a mixture consisting of 1.5 ml. of acetic acid, 1.5 ml. of water and 15 ml. of tetrahydrofuran. Add 1.25 g. of zinc dust and stir the mixture at 0°-5° C. Monitor the reaction by thin layer chromatography until the starting material is substantially all converted (approximately 1-hour). Filter, wash the solids with ethyl acetate and the filtrate with saturated sodium bicarbonate solution. Dry the filtrate over magnesium sulfate, filter and evaporate the filtrate to a residue. Crystallize the residue from the ethyl ether:methylene chloride to obtain the title compound of this Step as white needles.

Yield—0.5 g.

M.P. 83°-85°

$^1$H NMR (CDCl$_3$): 1.37(d,e,J=7),2.5-2.7(n,Z, exch by D$_2$O), 3.14 (m,2),3.73(dd,1,J=8.25),3.84(q,2,J=7),4.23(m,1),4.76(m,2),5.2-5.6(m,2),5.67(d,1,J=2.5) and 5.8-6.25(m.1).

(F)
Sodium-(5R,6S,8R)-2-(2-hydroxyethylthio)-6-(1-hydroxyethyl)-penem-3-carboxylate Dissolve 200 mg. of the produce of Step E in 4 ml. of methylene chloride, Dissolve 0.105 g of sodium 2-ethylhexanoate in 2 ml. of ethyl acetate, mix the two solutions. Add to the resulting solution 14 mg. of triphenylphosphine, 14 mg. of tetrakis (triphenylphosphine) palladium and stir the mixture at room temperature under nitrogen for 1 hour. Dilute the reaction mixture with 20 ml. of ethyl acetate and extract with water (3×10 ml). Pass a stream of nitrogen through the aqueous extract to remove residual organic solvents, filter and lyophilize the aqueous layer to obtain thereby the title compound as a pale brown powder.

Yield—190 mg.

$^1$H NMR (D$_2$O): 1.24(d,3,J=7),3.0(m,2),3.77(t,2,J=7),3.63(dd,1,J=6,2),4.15(m,1), and 5.60(d,1,J=2).

The potassium salt may be prepared by replacing sodium 2-ethylhexanoic acid with potassium 2-ethylhexanoic acid.

Alternatively, the potassium salt may be prepared from the sodium salt by methods known in the art such as replacement by ion exchange of an aqueous solution of the sodium salt. Similarily, metabolisable esters of formula I, e.g. the pivaloyloxymethyl and phthalidyl esters may be prepared from the sodium salts utilizing known procedures.

By replacing sodium 2-ethylhexanoate with an equivalent quantity of 2-ethylhexanoic acid, and by following the procedure of step F, (5R,6S,8R)-6-(1-hydroxyethyl)-2(2-hydroxyethylthio)-penem-3-carboxylic acid is produced.

By reacting sodium-(5R,6S,8R)-2-(2-hydroxyethylthio)-6-(1-hydroxyethyl)-penem-3-carboxylate with an equivalent amount of chloromethylpivalate in an aprotic solvent such as dimethylformamide or acetonitrile the corresponding pivaloyloxymethyl ester derivative is prepared; i.e. pivaloyloxymethyl (5R,6S,8R)-2-(2-hydroethylthio)-6-(1-hydroethyl)-penem-3-carboxylate.

In a similar manner, by reacting sodium-(5R,6S,8R)-2-(2-hydroxyethylthio)-6-(1-hydroxyethyl)-penem-3-carboxylate with an equivalent amount of bromophthalide in dimethylformamide or acetonitrile according to the procedure described above the corresponding phthalidyl ester derivative is prepared; i.e. phthalidyl (5R,6S,8R)-2-(2-hydroxyethylthio)-6-(1-hydroxyethyl)-penem-3-carboxylate.

The following formulations are to examplify some of the dosage forms in which the antibacterial agents of this invention may be employed. In each, the active ingredient is designated by the term "Drug" which is meant to indicate an equivalent quantity of one of the following compounds:

sodium (5R,6S,8R)-6-(1-hydroxyethyl)-2-(2-hydroxyethylthio)penem-3-carboxylate,
potassium (5R,6S,8R)-6-(1-hydroxyethyl)-2-(hydroxyethylthio)-penem-3-carboxylate.
phthalidyl (5R,6S,8R)-2-(2-hydroxyethylthio)-6-(1-hydroxyethyl)-penem-4-carboxylate, or pivaloyloxymethyl(5R,6S,8R)-2-(2-hydroxyethylthio)-6-(1-hydroxyethyl)-penem-3-carboxylate.

EXAMPLE 2

Injectable Formulation

Per vial:sodium or potassium (5R,6S,8R)-6-(1-hydroxyethyl)-2-(2-hydroxyethylthio)-penem-3-carboxylate (Sterile powder).

Exemplary unit dosages may be 125 mg., 250 mg., 500 mg., 1 gm. and 2 gms. Add sterile water for injection U.S.P. or bacteriostatic water for injection U.S.P., for reconstitution.

EXAMPLE 3

Capsule Formulation

| Item No. | Ingredient | mg/capsule | mg/capsule |
|---|---|---|---|
| 1 | Drug | 250 | 500 |
| 2 | Microcrystalline Cellulose | 30 | 60 |
| 3 | Corn Starch, Dried | 15 | 30 |
| 4 | Silica Gel | 4.5 | 9 |
| 5 | Magnesium Stearate | 0.5 | 1 |
|   |   | 300.0 mg | 600 mg |

Method

Mix Item Nos. 1,2,3 and 4 in a suitable mixer for 10-15 minutes. Add Item No. 5 and mix for 1-3 minutes. Fill the above mixture in two-piece hard gelatin capsules of required size. Alternatively, mix Item Nos. 1,2,3, and 4 in a suitable mixer for 10-15 minutes. Add half the amount of Item No. 5, mix for 1-3 minutes. Pass the mixture through a suitable compactor. Pass the compacted mixture through a suitable mill equipped with 16 mesh screen. Remix and add the remainder amount of Item No. 5. Mix for 1-3 minutes. Fill the above mixture in two-piece hard gelatin capsules of required size.

EXAMPLE 4

Tablet Formulation

| Item No. | Ingredient | mg/tablet | mg/tablet |
|---|---|---|---|
| 1 | Drug | 250 | 500 |
| 2 | Microcrystalline Cellulose | 100 | 200 |
| 3 | Corn Starch, Dried | 40 | 80 |
| 4 | Silica Gel | 6 | 12 |
| 5 | Magnesium Stearate | 4 | 8 |
|   |   | 400 mg | 800 mg |

Method

Mix Item Nos. 1, 3 and half the amount of Item No. 4 in a suitable mixer for 10-15 minutes. Add half the amount of Item No. 5 and mix for 1-3 minutes. Pass the mixture through a suitable compactor. (Alternatively, slug the mixture on a rotary tablet machine equipped with 1″ flat bevelled punches). Mill the compacted material or the slugs using a suitable milling machine equipped with 16 mesh screen. Remix. Add Item No. 2 and the remainder amount of Item No. 4. Mix for 10-15 minutes. Add the balance of Item No. 5 and mix for 1-3 minutes. Compress the mixture into the tablets of required shape and size on a rotary tablet machine. The tablets may be coated using standard coating procedures.

EXAMPLE 5

Topical Formulation

| Item No. | Ingredient | mg/g |
|---|---|---|
| 1 | Drug | 25 |
| 2 | Ethyl Alcohol | 400 |
| 3 | Hydroxypropyl Cellulose | 15 |
| 4 | Polyethylene Glycol 400 | 560 |

Mix Item Nos. 1, 2 and 4 in a suitable mixer. Stir vigorously and charge Item No. 3. Maintain stirring until uniformity is achieved.

EXAMPLE 6

Oral Powder for Reconstitution (I)

Part A (Powder Formulation)

| Item No. | Ingredient | mg/g |
|---|---|---|
| 1 | Drug | 46.3 |
| 2 | Flavor(s) | q.s. |
| 3 | Colorant | q.s. |
| 4 | Preservative | q.s. |
| 5 | Buffer Agents | q.s. |
| 6 | Sugar | q.s. |
| | To make | 1.0 g |

Mix Item Nos. 1,2,3,4 and 5 thoroughly. Charge Item No. 6 and mix until uniformity is achieved.

EXAMPLE 7

Oral Liquid

| Item No. | Ingredient | mg/ml |
|---|---|---|
| 1 | Drug | 25.0 |
| 2 | Sweetner | q.s. |
| 3 | Flavor | q.s. |
| 4 | Colorant | q.s. |
| 5 | Vegetable Oil | q.s. |
| | To make | 1.0 ml |

Charge 90% of Item No. 5 needed into a suitable container. Charge Item Nos. 1,2,3 and 4 and mix well. Bring to the final volume by the reserved Item No. 5.

I claim:

1. A compound of the formula

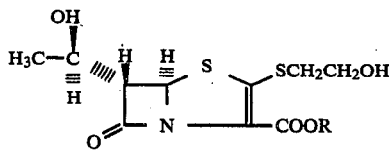

wherein R is a member of the group consisting of sodium or potassium cations, phthalidyl and pivaloyloxymethyl.

2. Sodium (5R,6S,8R)-2-(2-hydroxyethylthio)-6-(1-hydroxyethyl)-penem-3-carboxylate.

3. Potassium (5R,6S,8R)-2-(2-hydroxyethylthio)-6-(1-hydroxyethyl)-penem-3-carboxylate.

4. Phthalidyl (5R,6S,8R)-2-(2-hydroxyethylthio)-6-(1-hydroxyethyl)-penem-3-carboxylate.

5. Pivaloyloxymethyl (5R,6S,8R)-2-(2-hydroxyethylthio)-6-(1-hydroxyethyl)-penem-3-carboxylate.

6. A pharmaceutical composition comprising an antibacterially effective amount of a compound of claim 1 together with a non-toxic pharmaceutically acceptable carrier.

7. A composition which is an oral antibacterial dosage unit comprising a compound of claim 1 in an amount sufficient to be orally effective as a broad spectrum antibacterial, together with a non-toxic pharmaceutically acceptable carrier.

8. An oral dosage unit according to claim 7 which is solid.

9. A method of effectively treating a warm-blooded animal having a susceptible bacterial infection which comprises administering to said animal a non-toxic, antibacterially effective amount of a composition of claim 6.

10. A method according to claim 9 wherein the composition is administered orally.

* * * * *